DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED AUGUST 5, 1975

937 O.G. 12

T937,002
TREATMENT OF MASTITIS

Norman G. Baker, 169 Van Houten Ave., Wyckoff, N.J. 07481

Continuation of abandoned application Ser. No. 279,607, Aug. 10, 1972. This application Oct. 23, 1973, Ser. No. 408,366

Int. Cl. A61k *27/00*
U.S. Cl. 424—343
No Drawing. 9 Pages Specification

Glycols having from 3 to 4 carbon atoms and at least one terminal group are effective in the treatment of ungulate mastitis. Particularly useful is 1,3 butylene glycol (1,3-BG) which is administered in pharmacologically effective doses.